US012377280B2

(12) United States Patent
Giladi et al.

(10) Patent No.: US 12,377,280 B2
(45) Date of Patent: Aug. 5, 2025

(54) SELECTING VALUES OF PARAMETERS FOR TREATMENT USING TUMOR TREATING FIELDS (TTFIELDS)

(71) Applicant: Novocure GmbH, Root (CH)

(72) Inventors: Moshe Giladi, Haifa (IL); Reuven R. Shamir, Zichron Yalakov (IL); Kirill Stepovoy, Haifa (IL)

(73) Assignee: Novocure GmbH, Baar (CH)

( * ) Notice: Subject to any disclaimer, the term of this patent is extended or adjusted under 35 U.S.C. 154(b) by 425 days.

(21) Appl. No.: 18/090,075

(22) Filed: Dec. 28, 2022

(65) Prior Publication Data
US 2023/0218912 A1    Jul. 13, 2023

Related U.S. Application Data

(60) Provisional application No. 63/294,937, filed on Dec. 30, 2021.

(51) Int. Cl.
*A61N 1/40* (2006.01)
*A61N 1/36* (2006.01)

(52) U.S. Cl.
CPC ........... *A61N 1/40* (2013.01); *A61N 1/36002* (2017.08)

(58) Field of Classification Search
CPC ...................... A61N 1/36002; A61N 1/0476
See application file for complete search history.

(56) References Cited

U.S. PATENT DOCUMENTS

| | | |
|---|---|---|
| 6,868,289 B2 | 3/2005 | Palti |
| 7,016,725 B2 | 3/2006 | Palti |
| 7,089,054 B2 | 8/2006 | Palti |
| 7,136,699 B2 | 11/2006 | Palti |
| 7,333,852 B2 | 2/2008 | Palti |
| 7,467,011 B2 | 12/2008 | Palti |
| 7,519,420 B2 | 4/2009 | Palti |
| 7,565,205 B2 | 7/2009 | Palti |
| 7,565,206 B2 | 7/2009 | Palti |
| 7,599,745 B2 | 10/2009 | Palti |
| 7,599,746 B2 | 10/2009 | Palti |
| 7,706,890 B2 | 4/2010 | Palti |
| 7,715,921 B2 | 5/2010 | Palti |
| 7,805,201 B2 | 9/2010 | Palti |
| 7,890,183 B2 | 2/2011 | Palti et al. |
| 7,912,540 B2 | 3/2011 | Palti |

(Continued)

FOREIGN PATENT DOCUMENTS

WO    2020222020 A1    11/2020

OTHER PUBLICATIONS

International Search Report and Written Opinion issued in application PCT/IB2022/062847 dated Apr. 12, 2023.

*Primary Examiner* — Michael W Kahelin
(74) *Attorney, Agent, or Firm* — Potomac Law Group, PLLC

(57) ABSTRACT

Characteristics of alternating electric fields that will be applied to a target region in a subject's body can be selected by applying different sets of pulses between electrode elements positioned on opposite sides of the target region. Thermal responses to the different sets of pulses are determined. Based on these thermal responses, the system selects a set of characteristics for output pulses of alternating current that will (a) maximize peak current amplitude and (b) keep temperatures at the electrode elements below a threshold value.

18 Claims, 5 Drawing Sheets

(56) References Cited

U.S. PATENT DOCUMENTS

| | | |
|---|---|---|
| 7,917,227 B2 | 3/2011 | Palti |
| 8,019,414 B2 | 9/2011 | Palti |
| 8,027,738 B2 | 9/2011 | Palti |
| 8,170,684 B2 | 5/2012 | Palti |
| 8,175,698 B2 | 5/2012 | Palti et al. |
| 8,229,555 B2 | 7/2012 | Palti |
| RE43,618 E | 8/2012 | Palti |
| 8,244,345 B2 | 8/2012 | Palti |
| 8,406,870 B2 | 3/2013 | Palti |
| 8,447,395 B2 | 5/2013 | Palti et al. |
| 8,447,396 B2 | 5/2013 | Palti et al. |
| 8,465,533 B2 | 6/2013 | Palti |
| 8,706,261 B2 | 4/2014 | Palti |
| 8,715,203 B2 | 5/2014 | Paiti |
| 8,718,756 B2 | 5/2014 | Palti |
| 8,764,675 B2 | 7/2014 | Palti |
| 9,023,090 B2 | 5/2015 | Palti |
| 9,023,091 B2 | 5/2015 | Palti |
| 9,039,674 B2 | 5/2015 | Palti et al. |
| 9,056,203 B2 | 6/2015 | Palti et al. |
| 9,440,068 B2 | 9/2016 | Palti et al. |
| 9,655,669 B2 | 5/2017 | Palti et al. |
| 9,750,934 B2 | 9/2017 | Palti et al. |
| 9,910,453 B2 | 3/2018 | Wasserman et al. |
| 10,188,851 B2 | 1/2019 | Wenger et al. |
| 10,441,776 B2 | 10/2019 | Kirson et al. |
| 10,779,875 B2 | 9/2020 | Palti et al. |
| 10,967,167 B2 | 4/2021 | Hagemann et al. |
| 11,103,698 B2 | 8/2021 | Chang et al. |
| 11,191,956 B2 | 12/2021 | Giladi et al. |
| 2004/0176804 A1 | 9/2004 | Palti |
| 2006/0167499 A1 | 7/2006 | Palti |
| 2006/0276858 A1 | 12/2006 | Palti |
| 2007/0225766 A1 | 9/2007 | Palti |
| 2007/0239213 A1 | 10/2007 | Palti |
| 2009/0076366 A1 | 3/2009 | Palti |
| 2012/0029419 A1 | 2/2012 | Palti |
| 2012/0283726 A1 | 11/2012 | Palti |
| 2014/0330268 A1 | 11/2014 | Palti et al. |
| 2017/0120041 A1 | 5/2017 | Wenger et al. |
| 2017/0215939 A1 | 8/2017 | Palti et al. |
| 2017/0281934 A1 | 10/2017 | Gliadi et al. |
| 2018/0001075 A1 | 1/2018 | Kirson et al. |
| 2018/0008708 A1 | 1/2018 | Giladi et al. |
| 2018/0050200 A1 | 2/2018 | Wasserman et al. |
| 2018/0160933 A1 | 6/2018 | Urman et al. |
| 2018/0202991 A1 | 7/2018 | Giladi et al. |
| 2018/0280687 A1 | 10/2018 | Carter et al. |
| 2019/0008386 A1 | 1/2019 | Puryear et al. |
| 2019/0117956 A1 | 4/2019 | Wenger et al. |
| 2019/0117963 A1 | 4/2019 | Travers et al. |
| 2019/0224474 A1 | 7/2019 | Yang et al. |
| 2019/0298998 A1 | 10/2019 | Coleman et al. |
| 2019/0308016 A1 | 10/2019 | Wenger et al. |
| 2020/0001069 A1 | 1/2020 | Kirson et al. |
| 2020/0009376 A1 | 1/2020 | Chang et al. |
| 2020/0009377 A1 | 1/2020 | Chang et al. |
| 2020/0016067 A1 | 1/2020 | Gotlib et al. |
| 2020/0023179 A1 | 1/2020 | Bomzon et al. |
| 2020/0061360 A1 | 2/2020 | Hagemann et al. |
| 2020/0061361 A1 | 2/2020 | Hagemann et al. |
| 2020/0069937 A1 | 3/2020 | Naveh et al. |
| 2020/0078582 A1 | 3/2020 | Alon et al. |
| 2020/0108031 A1 | 4/2020 | Borst et al. |
| 2020/0114141 A1 | 4/2020 | Bomzon et al. |
| 2020/0114142 A1 | 4/2020 | Bomzon et al. |
| 2020/0121728 A1 | 4/2020 | Wardak et al. |
| 2020/0129761 A1 | 4/2020 | Bomzon et al. |
| 2020/0146586 A1 | 5/2020 | Naveh et al. |
| 2020/0155835 A1 | 5/2020 | Wasserman et al. |
| 2020/0171297 A1 | 6/2020 | Kirson et al. |
| 2020/0179512 A1 | 6/2020 | Giladi et al. |
| 2020/0219261 A1 | 7/2020 | Shamir et al. |
| 2020/0269037 A1 | 8/2020 | Hagemann et al. |
| 2020/0269041 A1 | 8/2020 | Zeevi et al. |
| 2020/0269042 A1 | 8/2020 | Giladi et al. |
| 2020/0269043 A1 * | 8/2020 | Wasserman .......... A61N 1/3787 |
| 2020/0368525 A1 | 11/2020 | Maag et al. |
| 2021/0031031 A1 | 2/2021 | Wasserman et al. |
| 2021/0038584 A1 | 2/2021 | Voloshin-Sela |
| 2021/0060334 A1 | 3/2021 | Avraham et al. |
| 2021/0069503 A1 | 3/2021 | Tran et al. |
| 2021/0138233 A1 | 5/2021 | Deslauriers |
| 2021/0162228 A1 | 6/2021 | Urman et al. |
| 2021/0177492 A1 | 6/2021 | Travers et al. |
| 2021/0187277 A1 | 6/2021 | Wasserman et al. |
| 2021/0196348 A1 | 7/2021 | Wasserman |
| 2021/0199640 A1 | 7/2021 | Patel et al. |
| 2021/0203250 A1 | 7/2021 | Wasserman |
| 2021/0268247 A1 | 9/2021 | Story et al. |
| 2021/0299440 A1 | 9/2021 | Deslauriers et al. |
| 2021/0308446 A1 | 10/2021 | Alon et al. |
| 2021/0330950 A1 | 10/2021 | Hagemann et al. |
| 2021/0346694 A1 | 11/2021 | Wasserman et al. |
| 2021/0379362 A1 | 12/2021 | Smith et al. |
| 2021/0408383 A1 | 12/2021 | Kalra et al. |
| 2022/0095997 A1 | 3/2022 | Wasserman |
| 2022/0096821 A1 | 3/2022 | Kirson et al. |
| 2022/0118249 A1 | 4/2022 | Bomzon et al. |
| 2022/0161028 A1 | 5/2022 | Giladi et al. |
| 2022/0193435 A1 | 6/2022 | Wasserman et al. |
| 2022/0267445 A1 | 8/2022 | Tran et al. |
| 2022/0280787 A1 | 9/2022 | Bomzon et al. |
| 2022/0288395 A1 | 9/2022 | Voloshin-Sela et al. |
| 2022/0313992 A1 | 10/2022 | Wasserman |
| 2022/0323753 A1 | 10/2022 | Voloshin-Sela et al. |
| 2022/0387784 A1 | 12/2022 | Kirson et al. |
| 2022/0395699 A1 | 12/2022 | Doyle |
| 2022/0409893 A1 | 12/2022 | Wasserman et al. |
| 2023/0000384 A1 | 1/2023 | Wasserman et al. |
| 2023/0001197 A1 | 1/2023 | Wasserman et al. |
| 2023/0001221 A1 | 1/2023 | Farber |
| 2023/0009366 A1 | 1/2023 | Voloshin-Sela et al. |
| 2023/0019638 A1 | 1/2023 | Wasserman |
| 2023/0037806 A1 | 2/2023 | Wasserman et al. |
| 2023/0043071 A1 | 2/2023 | Wasserman et al. |
| 2023/0098801 A1 | 3/2023 | Carlson |

* cited by examiner

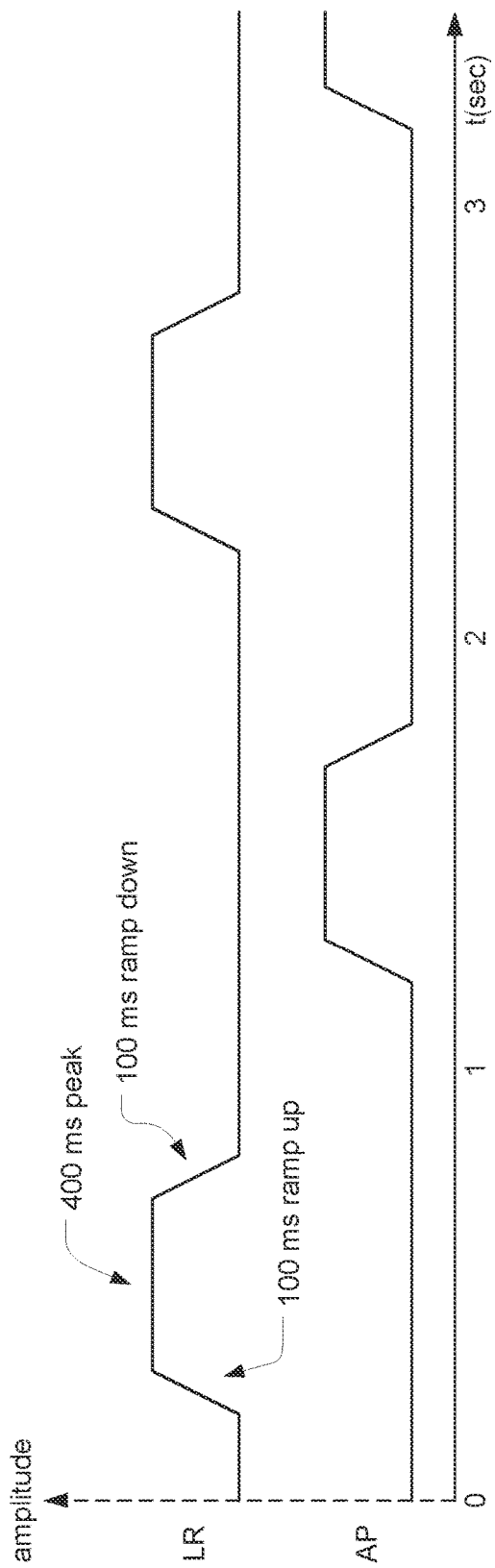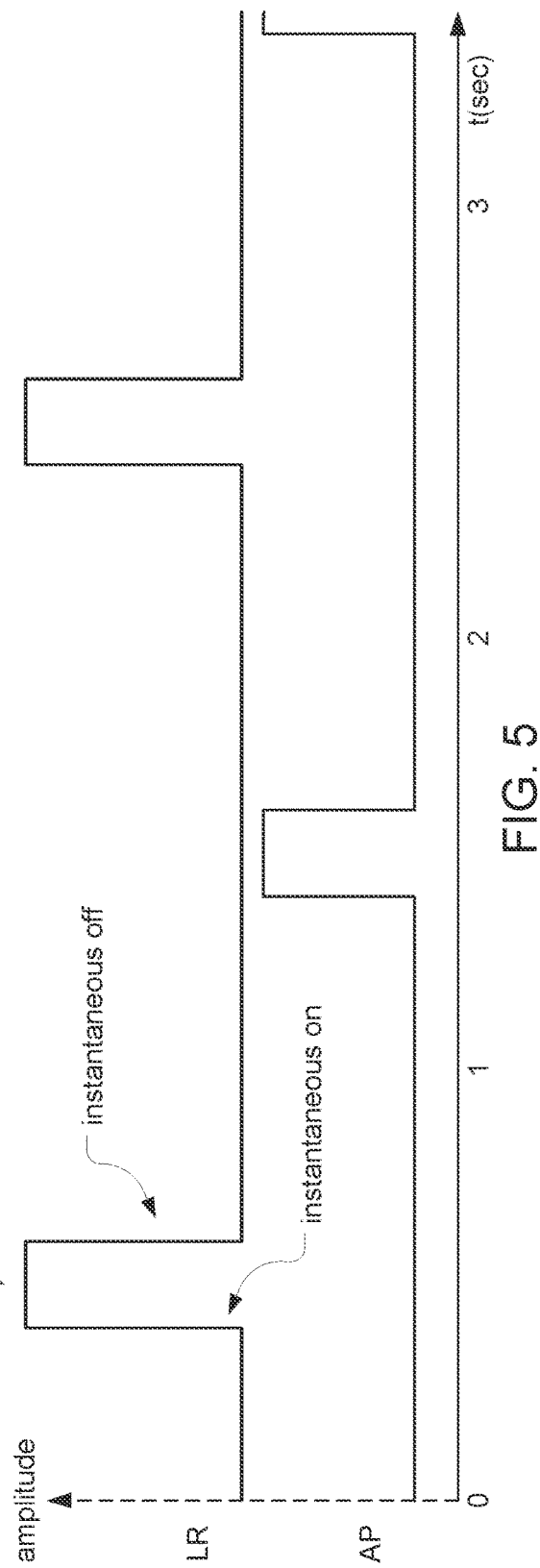

SELECTING VALUES OF PARAMETERS FOR TREATMENT USING TUMOR TREATING FIELDS (TTFIELDS)

CROSS REFERENCE TO RELATED APPLICATIONS

This application claims the benefit of U.S. Provisional Application 63/294,937, filed Dec. 30, 2021, which is incorporated herein by reference in its entirety.

BACKGROUND

Tumor Treating Fields (TTFields) therapy is a proven approach for treating tumors using alternating electric fields, e.g., at frequencies between 100-500 kHz (e.g., 150-200 kHz). See, for example, U.S. Pat. No. 7,565,205 (which is incorporated herein by reference in its entirety). Alternating electric fields at frequencies between 50 kHz and 1 MHz can also be used to treat medical conditions other than tumors. For example, as described in U.S. Pat. No. 10,967,167 (which is incorporated herein by reference in its entirety), alternating electric fields, e.g., at 50-200 kHz, can increase the permeability of the blood brain barrier so that, e.g., chemotherapy drugs can reach the brain. And as described in U.S. Pat. No. 11,103,698 (which is incorporated herein by reference in its entirety), alternating electric fields, e.g., at 50-500 kHz, can increase the permeability of cell membranes so that large molecules can traverse cell membranes.

FIG. 1 is a schematic representation of the prior art Optune® system for delivering TTFields. Four transducer arrays 90 are placed on the patient's skin in the vicinity of a tumor (e.g., a glioblastoma). Each transducer array 90 includes a plurality (e.g., between 9 and 20) capacitively coupled electrode elements, each of which has an electrically conductive substrate with a dielectric layer disposed thereon. The transducer arrays 90 are arranged in two pairs. The AC signal generator 95 (a) sends an AC current through one pair of arrays 90L, 90R for one second, which induces an electric field with a first direction through the tumor; then (b) sends an AC current through the other pair of arrays 90A, 90P for one second, which induces an electric field with a second direction through the tumor; then repeats steps (a) and (b) for the duration of the treatment. During any given one of these 1 second intervals, the amplitude of the AC signal ramps up for 50 (or 100) ms, remains constant for the next 900 (or 800) ms, then ramps down to zero for 50 (or 100) ms, as depicted in FIG. 2. When the Optune® system detects that one of its transducer arrays is getting too hot, it reduces the maximum AC voltage level at all its outputs to prevent overheating.

SUMMARY OF THE INVENTION

One aspect of the invention is directed to a first method of selecting characteristics of alternating electric fields that are applied to a target region in a subject's body. The first method comprises applying a plurality of first pulses of alternating current between at least one first electrode element and at least one second electrode element. The at least one first electrode element and the at least one second electrode element are positioned on opposite sides of the target region, and the plurality of first pulses has a first set of characteristics that includes a duration of each first pulse and a number of first pulses per minute. The first method also comprises determining first thermal responses to the plurality of first pulses at the at least one first electrode element and at the at least one second electrode element. The first method also comprises applying a plurality of second pulses of alternating current between the at least one first electrode element and the at least one second electrode element. The plurality of second pulses has a second set of characteristics that includes a duration of each second pulse and a number of second pulses per minute, and the first and second sets of characteristics are different. The first method also comprises determining second thermal responses to the plurality of second pulses at the at least one first electrode element and at the at least one second electrode element. And the first method also comprises selecting, based on the first and second sets of characteristics, the first thermal responses, and the second thermal responses, a set of characteristics for a plurality of first output pulses of alternating current that (a) maximizes peak current amplitude and (b) keeps temperatures at the at least one first electrode element and at the at least one second electrode element below a threshold value. The set of characteristics for the plurality of first output pulses includes a duration of each first output pulse and a number of first output pulses per minute.

In some instances of the first method, the first set of characteristics further includes a rise time of each first pulse, the second set of characteristics further includes a rise time of each second pulse, and the set of characteristics for the plurality of first output pulses further includes a rise time of each first output pulse.

Some instances of the first method further comprise positioning the at least one first electrode element on the subject's body, and positioning the at least second first electrode element on the subject's body.

In some instances of the first method, the selecting of the set of characteristics for the plurality of first output pulses is based on a calculation of heat transfer using the equation $$\frac{dQ}{dt} = h \cdot A(T_{body}(t) - T_{env}), \left[\frac{\text{Joule}}{\text{sec}}\right] \text{ or [Watt]}$$

where dQ/dt is the rate of heat transfer out of or into the body, h is the heat transfer coefficient [Watt/k·m$^2$], A is the heat transfer surface area [m$^2$], $T_{body}$ is the temperature of the object's surface, and $T_{env}$ is the temperature of the environment.

Some instances of the first method further comprise applying a plurality of fifth pulses of alternating current between the at the least one first electrode element and the at least one second electrode element, wherein the plurality of fifth pulses has a fifth set of characteristics that includes a duration of each fifth pulse and a number of fifth pulses per minute. These instances also further comprise determining fifth thermal responses to the plurality of fifth pulses at the at least one first electrode element and at the at least one second electrode element. The selecting of the set of characteristics for the plurality of first output pulses is further based on the fifth set of characteristics and the fifth thermal responses.

Another aspect of the invention is directed to a second method of selecting characteristics of alternating electric fields that are applied to a target region in a subject's body. The second method comprises applying a plurality of first pulses of alternating current between at least one first electrode element and at least one second electrode element. The at least one first electrode element and the at least one second electrode element are positioned on opposite sides of the target region, and the plurality of first pulses has a first set of characteristics that includes a duration of each first pulse and a number of first pulses per minute. The second method also comprises determining first thermal responses to the plurality of first pulses at the at least one first electrode element and at the at least one second electrode element. The second method also comprises applying a plurality of second pulses of alternating current between the at least one first electrode element and the at least one second electrode element. The plurality of second pulses has a second set of characteristics that includes a duration of each second pulse and a number of second pulses per minute, and the first and second sets of characteristics are different. The second method also comprises determining second thermal responses to the plurality of second pulses at the at least one first electrode element and at the at least one second electrode element. And the second method also comprises selecting, based on the first and second sets of characteristics, the first thermal responses, and the second thermal responses, a set of characteristics for a plurality of first output pulses of alternating current that (a) maximizes peak current amplitude and (b) keeps temperatures at the at least one first electrode element and at the at least one second electrode element below a threshold value. The set of characteristics for the plurality of first output pulses includes a duration of each first output pulse and a number of first output pulses per minute. The second method also comprises applying a plurality of third pulses of alternating current between at least one third electrode element and at least one fourth electrode element. The plurality of third pulses has a third set of characteristics that includes a duration of each third pulse and a number of third pulses per minute. The second method also comprises determining third thermal responses to the plurality of third pulses at the at least one third electrode element and at the at least one fourth electrode element, and applying a plurality of fourth pulses of alternating current between the at least one third electrode element and the at least one fourth electrode element. The plurality of fourth pulses has a fourth set of characteristics that includes a duration of each fourth pulse and a number of fourth pulses per minute, and the third and fourth sets of characteristics are different. The second method also comprises determining fourth thermal responses to the plurality of fourth pulses at the at least one third electrode element and at the at least one fourth electrode element. The second method also comprises selecting, based on the third and fourth sets of characteristics, the third thermal responses, and the fourth thermal responses, a set of characteristics for a plurality of second output pulses of alternating current that (a) maximizes peak current amplitude and (b) keeps temperatures at the at least one third electrode element and at the at least one fourth electrode element below a threshold value. The set of characteristics for the plurality of second output pulses includes a duration of each second output pulse and a number of second output pulses per minute.

In some instances of the second method, the number of first pulses per minute is the same as the number of third pulses per minute, the number of second pulses per minute is the same as the number of fourth pulses per minute, and the number of first output pulses per minute is the same as the number of second output pulses per minute.

In some instances of the second method, the first set of characteristics further includes a rise time of each first pulse, the second set of characteristics further includes a rise time of each second pulse, the third set of characteristics further includes a rise time of each third pulse, the fourth set of characteristics further includes a rise time of each fourth pulse, the set of characteristics for the plurality of first output pulses further includes a rise time of each first output pulse, and the set of characteristics for the plurality of second output pulses further includes a rise time of each second output pulse.

In some instances of the second method, an electric field that is induced by applying the plurality of first pulses of alternating current between the at least one first electrode element and the at least one second electrode element is within 15° of perpendicular from an electric field that is induced by applying the plurality of third pulses of alternating current between the at least one third electrode element and the at least one fourth electrode element.

Some instances of the second method further comprise applying a plurality of fifth pulses of alternating current between the at the least one first electrode element and the at least one second electrode element, wherein the plurality of fifth pulses has a fifth set of characteristics that includes a duration of each fifth pulse and a number of fifth pulses per minute. These instances also further comprise determining fifth thermal responses to the plurality of fifth pulses at the at least one first electrode element and at the at least one second electrode element. The selecting of the set of characteristics for the plurality of first output pulses is further based on the fifth set of characteristics and the fifth thermal responses.

Another aspect of the invention is directed to a first apparatus that selects characteristics of alternating electric fields that are applied to a target region in a subject's body. The first apparatus comprises an AC voltage generator having a first output configured to (a) apply a plurality of first pulses of alternating current between at least one first electrode element and at least one second electrode element, and (b) apply a plurality of second pulses of alternating current between the at least one first electrode element and the at least one second electrode element. The plurality of first pulses has a first set of characteristics that includes a duration of each first pulse and a number of first pulses per minute, and the plurality of second pulses has a second set of characteristics that includes a duration of each second pulse and a number of second pulses per minute. The first and second sets of characteristics are different. The first apparatus also comprises a controller configured to input data regarding first thermal responses to the plurality of first pulses at the at least one first electrode element and at the at least one second electrode element, and to input data regarding second thermal responses to the plurality of second pulses at the at least one first electrode element and at the at least one second electrode element. The controller is further configured to select, based on the first and second sets of characteristics, the first thermal responses, and the second thermal responses, a set of characteristics for a plurality of first output pulses of alternating current that (a) maximizes peak current amplitude and (b) keeps temperatures at the at least one first electrode element and at the at least one second electrode element below a threshold value. The set of characteristics for the plurality of first output pulses includes a duration of each first output pulse and a number of first output pulses per minute.

In some embodiments of the first apparatus, the first set of characteristics further includes a rise time of each first pulse, the second set of characteristics further includes a rise time of each second pulse, and the set of characteristics for the plurality of first output pulses further includes a rise time of each first output pulse.

In some embodiments of the first apparatus, the first output of the AC voltage generator is further configured to apply a plurality of fifth pulses of alternating current between the at the least one first electrode element and the at least one second electrode element, wherein the plurality of fifth pulses has a fifth set of characteristics that includes a duration of each fifth pulse and a number of fifth pulses per minute, and wherein the first, second, and fifth sets of characteristics are all different. In these embodiments, the controller is further configured to input data regarding fifth thermal responses to the plurality of fifth pulses at the at least one first electrode element and at the at least one second electrode element, and the controller's selection of the set of characteristics for the plurality of first output pulses is further based on the fifth set of characteristics and the fifth thermal responses.

In some embodiments of the first apparatus, the controller is further configured to select the set of characteristics for the plurality of first output pulses based on a calculation of heat transfer using the equation $$\frac{dQ}{dt} = h \cdot A(T_{body}(t) - T_{env}), \left[\frac{\text{Joule}}{\text{sec}}\right] \text{ or } [\text{Watt}]$$

dQ/dt where is the rate of heat transfer out of or into the body, where h is the heat transfer coefficient [Watt/k·m$^2$], where A is the heat transfer surface area [m$^2$], where $T_{body}$ is the temperature of the object's surface, and where $T_{env}$ is the temperature of the environment.

Another aspect of the invention is directed to a second apparatus that selects characteristics of alternating electric fields that are applied to a target region in a subject's body. The second apparatus comprises an AC voltage generator having a first output configured to (a) apply a plurality of first pulses of alternating current between at least one first electrode element and at least one second electrode element, and (b) apply a plurality of second pulses of alternating current between the at least one first electrode element and the at least one second electrode element. The plurality of first pulses has a first set of characteristics that includes a duration of each first pulse and a number of first pulses per minute, and the plurality of second pulses has a second set of characteristics that includes a duration of each second pulse and a number of second pulses per minute. The first and second sets of characteristics are different. The second apparatus also comprises a controller configured to input data regarding first thermal responses to the plurality of first pulses at the at least one first electrode element and at the at least one second electrode element, and to input data regarding second thermal responses to the plurality of second pulses at the at least one first electrode element and at the at least one second electrode element. The controller is further configured to select, based on the first and second sets of characteristics, the first thermal responses, and the second thermal responses, a set of characteristics for a plurality of first output pulses of alternating current that (a) maximizes peak current amplitude and (b) keeps temperatures at the at least one first electrode element and at the at least one second electrode element below a threshold value. The set of characteristics for the plurality of first output pulses includes a duration of each first output pulse and a number of first output pulses per minute. The AC voltage generator also has a second output configured to (a) apply a plurality of third pulses of alternating current between at least one third electrode element and at least one fourth electrode element, and (b) apply a plurality of fourth pulses of alternating current between the at least one third electrode element and the at least one fourth electrode element. The plurality of third pulses has a third set of characteristics that includes a duration of each third pulse and a number of third pulses per minute, and the plurality of fourth pulses has a fourth set of characteristics that includes a duration of each fourth pulse and a number of fourth pulses per minute. The third and fourth sets of characteristics are different. The controller is further configured to input data regarding third thermal responses to the plurality of third pulses at the at least one third electrode element and at the at least one fourth electrode element, and to input data regarding fourth thermal responses to the plurality of fourth pulses at the at least one third electrode element and at the at least one fourth electrode element. The controller is also further configured to select, based on the third and fourth sets of characteristics, the third thermal responses, and the fourth thermal responses, a set of characteristics for a plurality of second output pulses of alternating current that (a) maximizes peak current amplitude and (b) keeps temperatures at the at least one third electrode element and at the at least one fourth electrode element below a threshold value. The set of characteristics for the plurality of second output pulses includes a duration of each second output pulse and a number of second output pulses per minute.

In some embodiments of the second apparatus, the number of first pulses per minute is the same as the number of third pulses per minute, the number of second pulses per minute is the same as the number of fourth pulses per minute, and the number of first output pulses per minute is the same as the number of second output pulses per minute.

In some embodiments of the second apparatus, the first set of characteristics further includes a rise time of each first pulse, the second set of characteristics further includes a rise time of each second pulse, the third set of characteristics further includes a rise time of each third pulse, and the fourth set of characteristics further includes a rise time of each fourth pulse. In these embodiments, the set of characteristics for the plurality of first output pulses further includes a rise time of each first output pulse, and the set of characteristics for the plurality of second output pulses further includes a rise time of each second output pulse.

In some embodiments of the second apparatus, the first output of the AC voltage generator is further configured to apply a plurality of fifth pulses of alternating current between the at the least one first electrode element and the at least one second electrode element, wherein the plurality of fifth pulses has a fifth set of characteristics that includes a duration of each fifth pulse and a number of fifth pulses per minute, and wherein the first, second, and fifth sets of characteristics are all different. In these embodiments, the controller is further configured to input data regarding fifth thermal responses to the plurality of fifth pulses at the at least one first electrode element and at the at least one second electrode element. And the controller's selection of the set of characteristics for the plurality of first output pulses is further based on the fifth set of characteristics and the fifth thermal responses.

BRIEF DESCRIPTION OF THE DRAWINGS

FIGS. 4 and 5 depict two examples of how the characteristics of the pulses of alternating current can be varied.

Various embodiments are described in detail below with reference to the accompanying drawings, wherein like reference numerals represent like elements.

DESCRIPTION OF THE PREFERRED EMBODIMENTS

Figure 1:
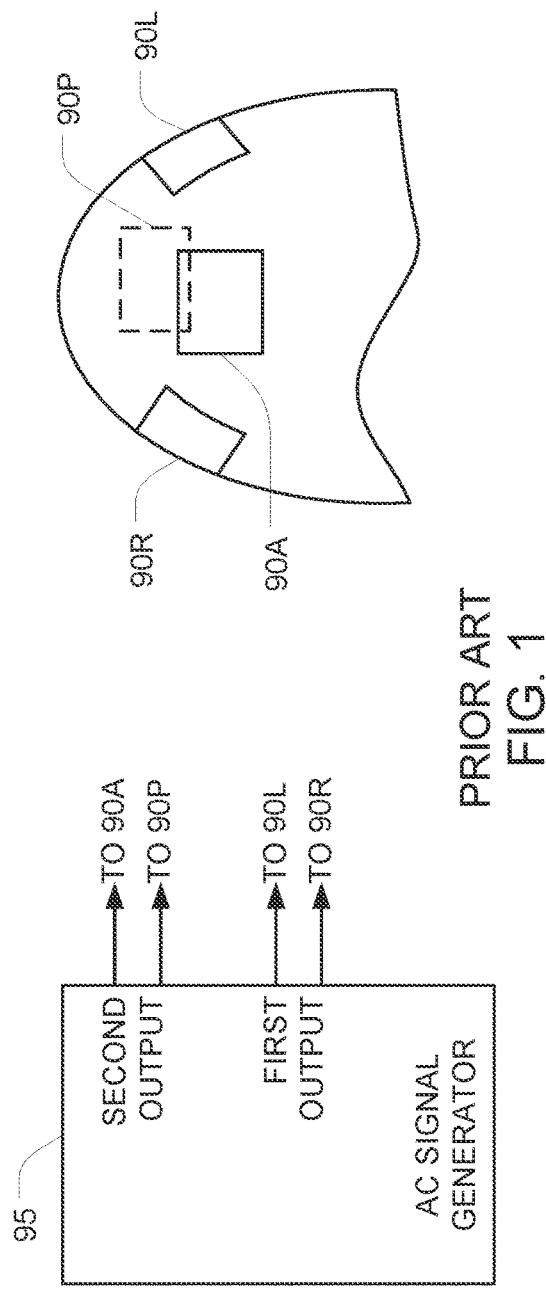
FIG. 1 is a schematic representation of the prior art Optune® system for delivering TTFields.
Figure 2:
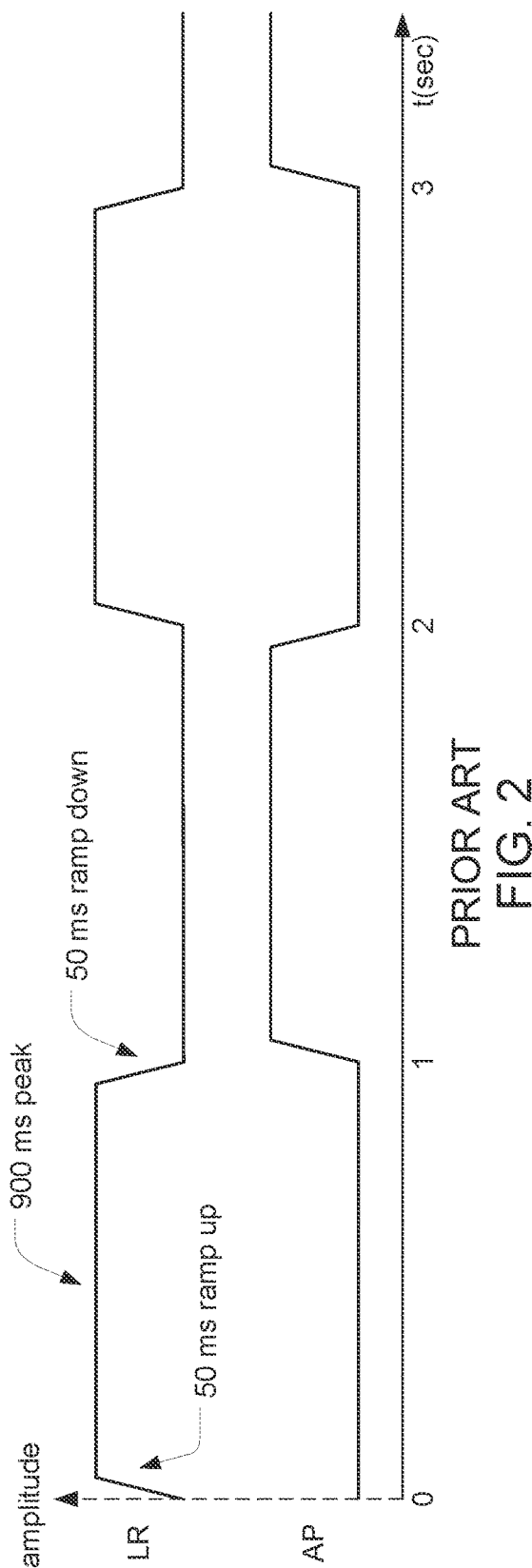
FIG. 2 depicts the amplitudes of output waveforms generated by the prior art Optune® system.

A set of parameters can be used to describe the alternating electric fields that are applied to a subject's body to treat a tumor (or for other purposes like increasing the permeability of the blood brain barrier). These parameters include, for example, the frequency of the alternating electric fields, the strength of the alternating electric fields (e.g., measured in V/cm), the power density of the alternating electric fields, the length of the time window that alternating electric fields are applied before the direction of the field is switched, the percentage of time during each of those windows that the alternating electric fields are on, and the ramp-up and ramp-down times during each of those windows.

When treating a subject using alternating electric fields, higher peak current amplitudes are associated with higher efficacy of treatment. But ordinarily, the alternating electric fields cannot be applied at their maximum current full-time because that may cause overheating of one or more of the electrodes that are used to apply the alternating electric fields.

It is very difficult (and perhaps impossible) to predict or simulate the amount of heating that will occur at each individual electrode element in each electrode array that is used to apply alternating electric fields to a subject's body. This is because the heating that occurs at any given electrode element is a function of at least (a) the parameters of the alternating electric fields themselves (e.g., those identified above), and (b) a large set of additional factors, many of which are subject-specific. Examples of the latter include, but are not limited to: (1) the position of the electrode elements with respect to the subject's body and with respect to the tumor, (2) the electrical conductivity of each voxel of tissue (including tumor tissue and healthy tissue) through which the alternating electric fields travel, (3) the electrical conductivity of the interface between the electrode element and the subject's body (which may depend, for example, on the condition of a hydrogel layer disposed beneath the electrode and/or how much sweat is present on the subject's body), (4) the flow rate of blood (which can carry heat away from the electrodes) in the vicinity of the electrode element, and (5) whether the electrode elements are covered by clothing or bedding.

The embodiments described herein overcome the difficult nature of simulating the amount of heating that will occur at each individual electrode element by taking actual measurements of the amount of heating that occurs at each individual electrode element after the electrode elements are positioned on the actual subject's body. Alternating electric fields with a first set of characteristics (e.g., pulse rate, pulse duration, etc.) are applied for a first interval of time (e.g., 30 s), and the thermal responses to those pulses is measured while the electrode elements remain positioned on the actual subject's body. Then, alternating electric fields with different characteristics are applied during one or more subsequent intervals of time, and the thermal responses to those different pulses are measured while the electrode elements remain positioned on the actual subject's body. Based on the characteristics of the signals that were applied and the thermal responses to those signals, the system determines the set of characteristics (e.g., the values of the various parameters) that should be used to apply alternating electric fields to the subject.

A variety of approaches may be used to determine the set of characteristics that should be used. One suitable approach is referred to herein as "the brute force approach." This approach involves testing a relatively large number of combinations of characteristics (e.g., 25-50 different combinations), observing the resulting thermal responses to each combination, and selecting the combination of characteristics that actually (a) maximized peak current amplitude and (b) kept temperatures below a threshold value.

Another suitable approach is referred to herein as "the intelligent approach." This approach involves testing fewer combinations of characteristics, and observing the resulting thermal response to each combination. Then, based on the observed results, the system calculates the combination of characteristics that is expected to (a) maximize peak current amplitude and (b) keep temperatures below a threshold value.

Figure 3:
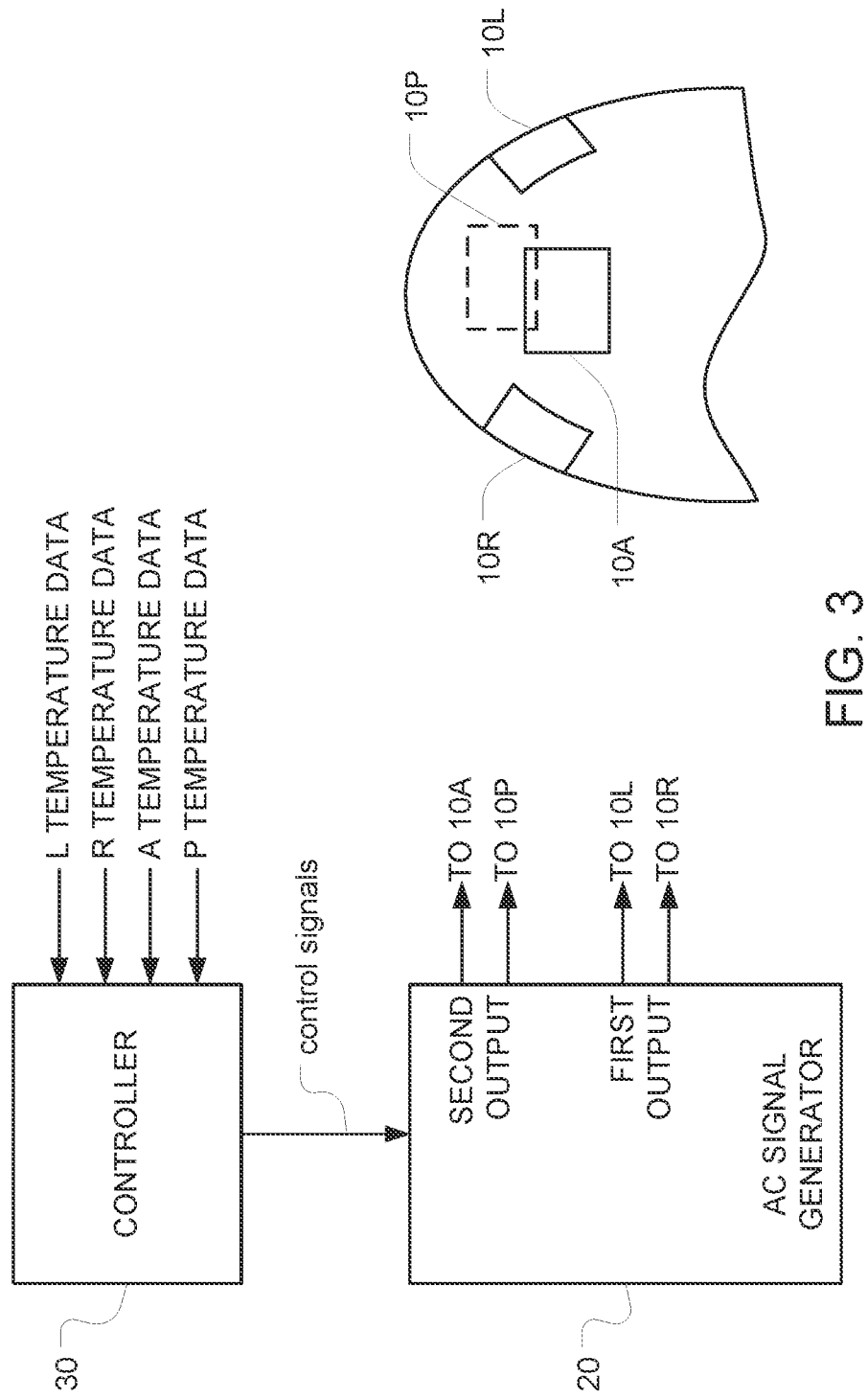
FIG. 3 is a block diagram of a system for selecting the set of characteristics for output pulses of alternating current that maximizes peak current amplitude and keeps temperatures at the electrode elements below a threshold value.

FIG. 3 is a block diagram of a system that can implement both the brute force approach and the intelligent approach, as well as other approaches for selecting the set of characteristics for the output pulses of alternating current that (a) maximizes peak current amplitude and (b) keeps temperatures at the electrode elements below a threshold value.

Four sets of electrode elements 10 are placed on the patient's skin in the vicinity of the target region. In some embodiments, each set of electrodes 10 includes a plurality (e.g., between 9 and 20) electrode elements, but in other embodiments, each set of electrode elements 10 may include only a single electrode element. Each electrode element may be capacitively coupled (as in the prior art Optune® system) or conductive.

In the FIG. 3 embodiment, the sets of electrode elements 10 are arranged in two pairs, and the AC signal generator 20 has two outputs. The first output is connected to the left and right (L/R) pair of sets 10L, 10R; and the second output is connected to the anterior and posterior pair (A/P) of sets 10A, 10P. When the AC signal generator 20 sends AC current through the L/R pair of sets 10L, 10R an electric field with a first direction is induced through the target region. When the AC signal generator 20 sends an AC current through the A/P pair of sets 10A, 10P an electric field with a second direction is induced through the target region.

The AC signal generator 20 has the ability to generate output pulses of AC with different characteristics, including but not limited to the number of output pulses per minute, the duration of each pulse, and the amplitude of each pulse. Optionally, the AC signal generator 20 also has the ability to vary other parameters of the output pulses such as the rise time and fall time of each pulse. By issuing appropriate control signals at appropriate times, a controller 30 causes the AC signal generator 20 to output AC signals with desired characteristics at the AC signal generator's first and second outputs at corresponding times. The AC signal generator 20 is designed to respond to the control signals that arrive from the controller 30.

Each set of electrode elements 10 also includes temperature sensors (not shown). Data from these temperature sensors is collected by the controller 30.

The controller 30 may be programmed to cause the AC signal generator 20 to alternate between outputting pulses of AC on the first output and outputting pulses of AC on the second output just like the prior art Optune® system described above. But unlike the prior art Optune® system, the number of pulses per minute, the duration of each pulse, the rise time of each pulse, and the fall time of each pulse are not all fixed in advance (i.e., predetermined).

FIGS. 4 and 5 depict some examples of how the characteristics of the pulses of alternating current can be varied. More specifically, both the upper and lower traces of FIG. 4 depict pulses that are generated at a pulse rate of 30 pulses per second for the L/R and A/P channels, respectively. Each pulse includes a 100 ms ramp up interval, a 400 ms interval during which the amplitude remains constant, and a 100 ms ramp-down interval, which collectively add up to a duration of 600 ms for each pulse. The controller 30 can vary any of these intervals by issuing appropriate control signals to the AC signal generator 20. Note that while the characteristics of the pulses for the L/R channel are the same as the characteristics of the pulses for the A/P channel in the example depicted in FIG. 4, that need not be the case. For example, the pulses for the L/R channel could have longer or shorter durations, longer or shorter rise times, and/or longer or shorter fall times than the pulses for the A/P channel.

The upper and lower traces of FIG. 5 depict another example of pulses that are generated at a pulse rate of 30 pulses per second for the L/R and A/P channels, respectively. In this example, the pulses for both channels jump immediately from the off state to their full amplitude, remain at that full amplitude for 200 ms, then switch off. Thus, the duration of each pulse is 200 ms, the ramp up interval is 0 ms, and the ramp down interval is 0 ms. Note that while the duration of the pulses for the AP channel are the same as duration of the pulses for the A/P channel, that need not be the case. For example, the pulses for the L/R channel could be longer or shorter than the pulse for the A/P channel.

In addition to controlling the shape envelope of the of the output pulses as described above in connection with FIGS. 4 and 5, the AC signal generator 20 has the ability to vary the amplitude of its outputs based on control signals that arrive from the controller 30. This is illustrated schematically in FIG. 5, where the amplitude of the AC pulses that are applied to the L/R channel is larger than the amplitude of the AC pulses that are applied to the A/P channel.

In the examples depicted in FIGS. 4 and 5, the output switches between L/R and A/P every 1 second, which means that the direction of the field will switch between L/R and A/P at that same rate. But in alternative embodiments, this direction-switching can occur at a different rate (e.g., between 0.1 s and 1 s, or between 1 s and 60 s). Moreover, the direction-switching rate need not be uniform across the L/R and A/P channels. For example, the system could alternate between activating the L/R output for 1 second and activating the A/P output for half a second.

The traces depicted in FIGS. 4 and 5 depict the amplitude of the AC pulses that are applied to the L/R and A/P channels as an unsigned magnitude on a relatively long timescale (i.e., longer than 10 ms). But because the output pulses generated by the signal generator 20 are AC pulses, the instantaneous output voltage at those outputs will alternate between positive and negative on a much shorter time scale (i.e., shorter than 0.1 ms), as described immediately below in connection with FIGS. 6A and 6B.

Figure 6A:
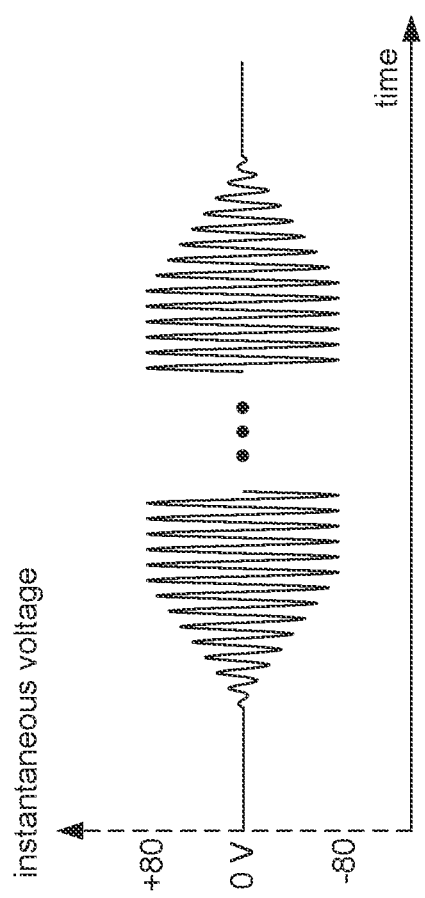
FIG. 6A is a schematic representation of the instantaneous output voltage associated with the waveform depicted in FIG. 4.
Figure 6B:
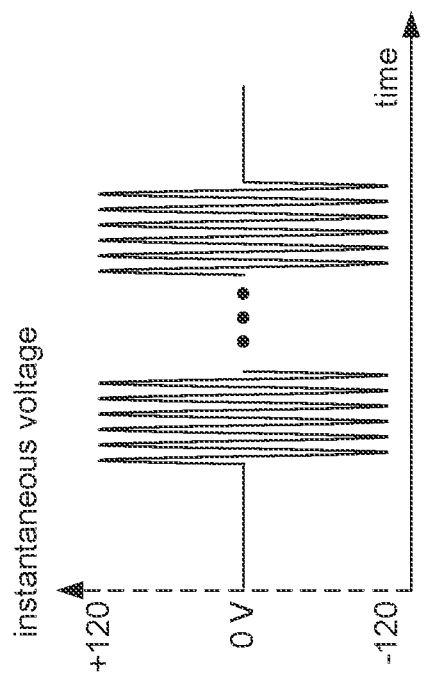
FIG. 6B is a schematic representation of the instantaneous output voltage associated with the waveform depicted in FIG. 5.

FIG. 6A depicts the instantaneous output voltage generated by the signal generator 20 when the output pulses ramp up to a set value and subsequently ramp down from that set value (as described above in connection with FIG. 4). And FIG. 6B depicts the instantaneous output voltage generated by the signal generator 20 when the output pulses jump up instantaneously to a set value and subsequently switch off instantaneously (as described above in connection with FIG. 5).

Figure 7:
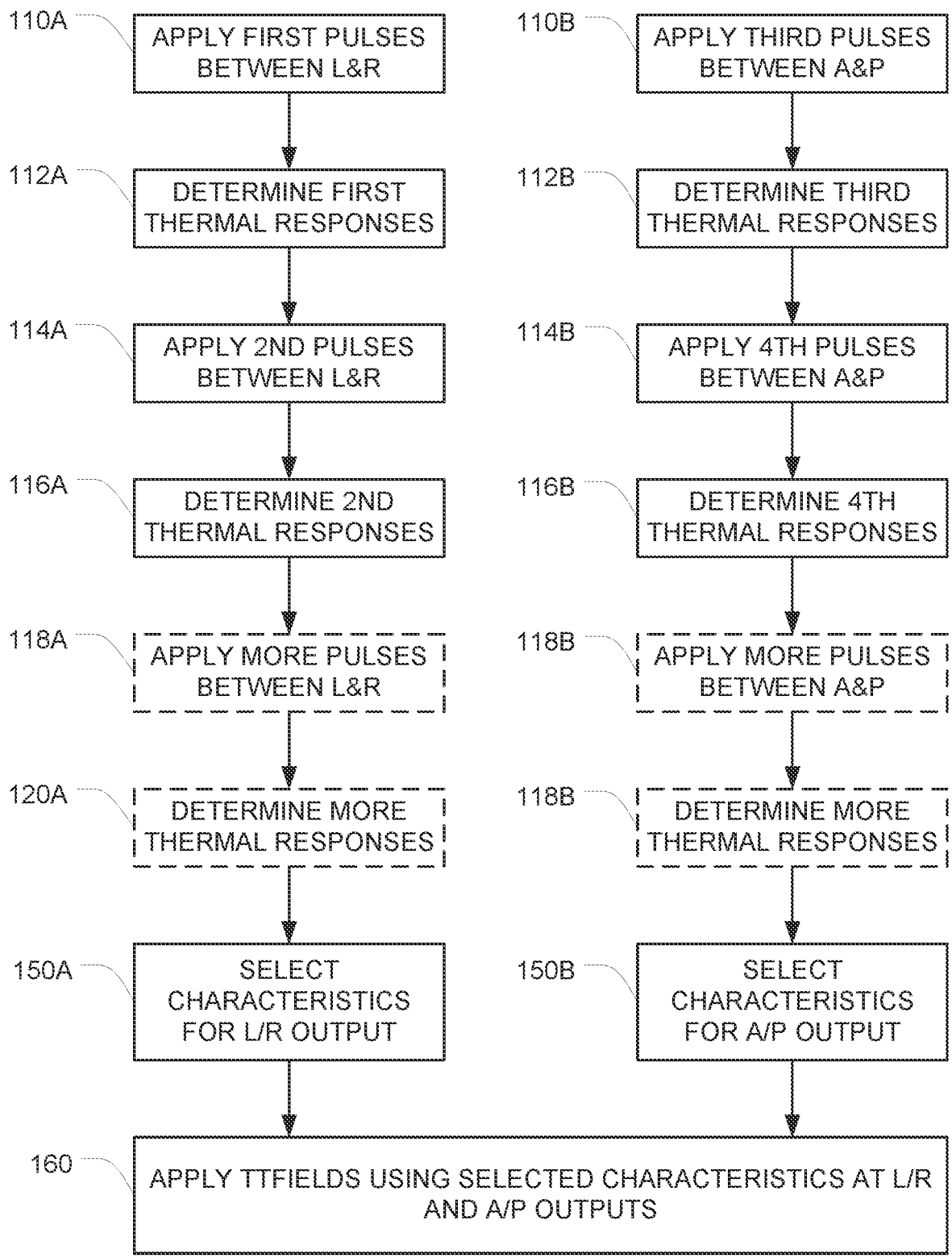
FIG. 7 is a flowchart of steps that may be performed to select characteristics for the output pulses that are generated by the AC signal generator in the FIG. 3 embodiment.

FIG. 7 is a flowchart of the steps that are orchestrated by the controller 30 (shown in FIG. 3) in order to select characteristics for the output pulses that are generated by the AC signal generator 20. More specifically, steps 110A-150A on the left side of FIG. 7 depicts how the characteristics for the L/R output of the signal generator 20 are selected, and steps 110B-150B (on the right side of FIG. 7) depict how the characteristics for the A/P output of the signal generator 20 are selected. After the characteristics for both channels are selected, alternating electric fields (e.g., TTFields) are applied using the selected characteristics at the L/R and A/P output in step 160.

Note that steps 110A-150A on the left can proceed independently from steps 110B-150B on the right (e.g., with steps 110A-150A coming before, after, or interleaved in time with steps 110B-150B). Moreover, in situations where the electric field can be applied in a single direction, only a single channel is necessary, in which case the steps for the omitted second channel are not performed. It is understood that while the L/R channel is referred to herein as the first channel, either the L/R or the A/P channel could correspond to the first channel and the other would then correspond to the second channel. Accordingly, either one of the L/R and the A/P channel could be omitted in situations where the electric field can be applied in a single direction.

Processing for the L/R channel begins at step 110A, where a plurality of first pulses of alternating current is applied between at least one first electrode element 90L and at least one second electrode element 90P, which are positioned on opposite sides of the target region. The characteristics for the plurality of first pulses include a duration of each first pulse and a number of first pulses per minute. After the plurality of first pulses have been applied for a sufficient amount of time so that thermal measurements can be made (e.g., after 30-60 seconds), processing proceeds to step 112A, where the thermal responses to the plurality of first pulses are determined (e.g., by making measurements using thermistors) at the at least one first electrode element 90L and at the at least one second electrode element 90R.

Next, in step 114A, a plurality of second pulses of alternating current are applied between the at least one first electrode element 90L and the at least one second electrode element 90R. The characteristics for the plurality of second pulses include a duration of each second pulse and a number of second pulses per minute, and at least one of those characteristics differs from the corresponding characteristic of the first pulses. After the plurality of second pulses have been applied for a sufficient amount of time so that thermal measurements can be made (e.g., after 30-60 seconds), processing proceeds to step 116A, where the thermal responses to the plurality of second pulses are determined (e.g., by making measurements using thermistors) at the at least one first electrode element 90L and at the at least one second electrode element 90R.

Optionally, after completing steps 110A-116A, an additional set of pulses of alternating current may be applied between the at least one first electrode element 90L and the at least one second electrode element 90R in step 118A. The characteristics for the additional pulses include a duration of each pulse and a number of pulses per minute, and at least one of those characteristics differs from the corresponding characteristic of the previous sets of pulses. After the additional pulses have been applied for a sufficient amount of time so that thermal measurements can be made (e.g., after 30-60 seconds), processing proceeds to step 120A, where the thermal responses to the additional pulses are determined (e.g., by making measurements using thermistors) at the at least one first electrode element 90L and at the at least one second electrode element 90R. Any number of these optional steps 118A-120A may be added at this point in the processing flow to ascertain the thermal response to a variety of different types of pulses. Typically, when the brute force approach is used, a relatively large number of optional steps will be added (e.g., to try out 25-50 different combinations). In contrast, when the intelligent approach is used, the number of optional steps that are added will be either zero or relatively small (e.g., less than 10).

Next, in step 150A, based on the first and second sets of characteristics (and optionally any number of additional sets of characteristics), the first thermal responses and the second thermal responses (and optionally any number of additional thermal responses), a set of characteristics for a plurality of first output pulses of alternating current is selected. This set of characteristics includes a duration of each first output pulse and a number of first output pulses per minute. The selection is made to (a) maximize peak current amplitude and (b) keep temperatures at the at least one first electrode element 90L and at the at least one second electrode element 90R below a threshold value.

How the selection in step 150A is made will depend on the approach used. For example, if the brute force approach is used, the selection of characteristics will be based on whichever set of pulses that were tested in steps 110A, 114A, and 118A resulted in the highest peak current amplitude without exceeding the temperature threshold (as measured in steps 112A, 116A, and 120A). Alternatively, if the intelligent approach is used, the selection of characteristics will be calculated based on the measurements made in steps 112A and 116A (and optionally 120A) and knowledge of the characteristics of the pulses that were applied in steps 110A and 114A (and optionally 118A). More specifically, the calculation predicts the combination of characteristics that is expected to (a) maximize peak current amplitude and (b) keep temperatures below a threshold value. Notably, when the intelligent approach is used, the selection of characteristics may not match any of the characteristics that were actually applied in steps 110A, 114A, and 118A.

One suitable algorithm for implementing the intelligent approach is described below. This approach obtains the desired results based on a relatively small number of thermal experiments. Parameters of the alternating electric fields that are applied in each of the experiments vary from experiment to experiment.

This algorithm relies on fitting a model to the obtained thermal results. This may be accomplished, for example, by fitting the data to a suitable function. One example of a suitable function is a 2D second-degree polynomic function e.g., $$a+bx+cx^2+d+ey+fy^2+gxy+hyxy^2+kx^2y$$

another example of a suitable function is a 2D Gaussian function, e.g., $$f(x, y) = A\exp\left(-\left(\frac{(x-x_o)^2}{2\sigma_X^2} + \frac{(y-y_o)^2}{2\sigma_Y^2}\right)\right) + \text{offset}$$

In some situations, the maximum current amplitude that is predicted by the model will coincide with a measured data point (i.e., the current that was actually observed when one of the sets of pulses were applied). But in other situations, the maximum current amplitude that is predicted by the model will not coincide with a measured data point.

Another approach for fitting a model to the obtained results is to rely on the Taguchi method, which is a step-by-step method for providing an estimate of the best parameters to use based on a predefined set of experiments with specific parameter values.

Optionally, additional characteristics (i.e., characteristics besides duration of each pulse and the number of pulses per minute) may be considered. Examples of such characteristics include the rise time of each first pulse and the rise time of each second pulse. When these additional characteristics are considered, additional characteristics for the output pulses may be selected (e.g., the rise time of the output pulses).

Note that in order to select the characteristics of the output pulses that should be used to treat a given patient, the at least one first electrode element 90L and the at least one second electrode element 90R should be positioned on the subject's body before steps 110A-150A are implemented.

Steps 110B-150B are similar to steps 110A-150A described above, except that the former corresponds to the A/P channel (and a set of characteristics for the plurality of second output pulses), while the latter corresponds to the L/R channel (and a set of characteristics for the plurality of first output pulses).

After the characteristics for the L/R output and the A/P output have been selected in steps 150A and 150B, an electric field is induced through the subject's body in step 160 by applying the plurality of first pulses of alternating current between the at least one first electrode element 90L and the at least one second electrode element 90R. in some embodiments, the direction of the resulting field is configured to be within 15° of perpendicular from an electric field that is induced by applying pulses of alternating current between the at least one third electrode element 90A and the at least one fourth electrode element 90P.

FIG. 7 only explicitly shows determining thermal responses when three different sets of pulses (with different characteristics) are applied. But thermal responses can be determined when additional sets of pulses with different characteristics are applied, by adding additional sets of the optional steps 118 and 120.

Optionally, the selection of the set of characteristics for the plurality of first output pulses may be based on a calculation of heat transfer that uses the equation $$\frac{dQ}{dt} = h \cdot A(T_{body}(t) - T_{env}), \left[\frac{\text{Joule}}{\text{sec}}\right] \text{ or } [\text{Watt}]$$

where dQ/dt is the rate of heat transfer out of or into the body, h is the heat transfer dt coefficient [Watt/k·m²], A is the heat transfer surface area [m$^2$], $T_{body}$ is the temperature of the object's surface, and $T_{env}$ is the temperature of the environment.

Finally, the use of step identifiers such as (a), (b), (c), etc. does not imply that the steps are performed in an alphabetical sequence. To the contrary, for example, a step labeled (a) could be implemented before, during, or after a step labeled (c).

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. A method of selecting characteristics of alternating electric fields that are applied to a target region in a subject's body, the method comprising:
    applying a plurality of first pulses of alternating current between at least one first electrode element and at least one second electrode element, wherein the at least one first electrode element and the at least one second electrode element are positioned on opposite sides of the target region, and wherein the plurality of first pulses has a first set of characteristics that includes a duration of each first pulse and a number of first pulses per minute;
    determining first thermal responses to the plurality of first pulses at the at least one first electrode element and at the at least one second electrode element;
    applying a plurality of second pulses of alternating current between the at least one first electrode element and the at least one second electrode element, wherein the plurality of second pulses has a second set of characteristics that includes a duration of each second pulse and a number of second pulses per minute, and wherein the first and second sets of characteristics are different;
    determining second thermal responses to the plurality of second pulses at the at least one first electrode element and at the at least one second electrode element; and
    selecting, based on the first and second sets of characteristics, the first thermal responses, and the second thermal responses, a set of characteristics for a plurality of first output pulses of alternating current that (a) maximizes peak current amplitude and (b) keeps temperatures at the at least one first electrode element and at the at least one second electrode element below a threshold value,
    wherein the set of characteristics for the plurality of first output pulses includes a duration of each first output pulse and a number of first output pulses per minute.

2. The method of claim 1,
    wherein the first set of characteristics further includes a rise time of each first pulse,
    wherein the second set of characteristics further includes a rise time of each second pulse, and
    wherein the set of characteristics for the plurality of first output pulses further includes a rise time of each first output pulse.

3. The method of claim 1, further comprising:
    positioning the at least one first electrode element on the subject's body; and
    positioning the at least second first electrode element on the subject's body.

4. The method of claim 1, further comprising:
    applying a plurality of third pulses of alternating current between at least one third electrode element and at least one fourth electrode element, wherein the plurality of third pulses has a third set of characteristics that includes a duration of each third pulse and a number of third pulses per minute;
    determining third thermal responses to the plurality of third pulses at the at least one third electrode element and at the at least one fourth electrode element;
    applying a plurality of fourth pulses of alternating current between the at least one third electrode element and the at least one fourth electrode element, wherein the plurality of fourth pulses has a fourth set of characteristics that includes a duration of each fourth pulse and a number of fourth pulses per minute, and wherein the third and fourth sets of characteristics are different;
    determining fourth thermal responses to the plurality of fourth pulses at the at least one third electrode element and at the at least one fourth electrode element; and
    selecting, based on the third and fourth sets of characteristics, the third thermal responses, and the fourth thermal responses, a set of characteristics for a plurality of second output pulses of alternating current that (a) maximizes peak current amplitude and (b) keeps temperatures at the at least one third electrode element and at the at least one fourth electrode element below a threshold value,
    wherein the set of characteristics for the plurality of second output pulses includes a duration of each second output pulse and a number of second output pulses per minute.

5. The method of claim 4, wherein the number of first pulses per minute is the same as the number of third pulses per minute, wherein the number of second pulses per minute is the same as the number of fourth pulses per minute, and wherein the number of first output pulses per minute is the same as the number of second output pulses per minute.

6. The method of claim 4,
    wherein the first set of characteristics further includes a rise time of each first pulse,
    wherein the second set of characteristics further includes a rise time of each second pulse,
    wherein the third set of characteristics further includes a rise time of each third pulse,
    wherein the fourth set of characteristics further includes a rise time of each fourth pulse,
    wherein the set of characteristics for the plurality of first output pulses further includes a rise time of each first output pulse, and
    wherein the set of characteristics for the plurality of second output pulses further includes a rise time of each second output pulse.

7. The method of claim 4, wherein an electric field that is induced by applying the plurality of first pulses of alternating current between the at least one first electrode element and the at least one second electrode element is within 15° of perpendicular from an electric field that is induced by applying the plurality of third pulses of alternating current between the at least one third electrode element and the at least one fourth electrode element.

8. The method of claim 4, further comprising:
    applying a plurality of fifth pulses of alternating current between the at the least one first electrode element and the at least one second electrode element, wherein the plurality of fifth pulses has a fifth set of characteristics that includes a duration of each fifth pulse and a number of fifth pulses per minute; and determining fifth thermal responses to the plurality of fifth pulses at the at least one first electrode element and at the at least one second electrode element, wherein the selecting of the set of characteristics for the plurality of first output pulses is further based on the fifth set of characteristics and the fifth thermal responses.

9. The method of claim 1, wherein the selecting of the set of characteristics for the plurality of first output pulses is based on a calculation of heat transfer using the equation $$\frac{dQ}{dt} = h \cdot A(T_{body}(t) - T_{env}), \left[\frac{\text{Joule}}{\text{sec}}\right] \text{ or [Watt]}$$

wherein dQ/dt is the rate of heat transfer out of or into the body,
wherein h is the heat transfer coefficient [Watt/k·m$^2$],
wherein A is the heat transfer surface area [m$^2$],
wherein $T_{body}$ is the temperature of the object's surface, and
wherein $T_{env}$ is the temperature of the environment.

10. The method of claim 1, further comprising:
applying a plurality of fifth pulses of alternating current between the at the least one first electrode element and the at least one second electrode element, wherein the plurality of fifth pulses has a fifth set of characteristics that includes a duration of each fifth pulse and a number of fifth pulses per minute; and
determining fifth thermal responses to the plurality of fifth pulses at the at least one first electrode element and at the at least one second electrode element,
wherein the selecting of the set of characteristics for the plurality of first output pulses is further based on the fifth set of characteristics and the fifth thermal responses.

11. An apparatus that selects characteristics of alternating electric fields that are applied to a target region in a subject's body, the apparatus comprising:
an AC voltage generator having a first output configured to (a) apply a plurality of first pulses of alternating current between at least one first electrode element and at least one second electrode element, wherein the plurality of first pulses has a first set of characteristics that includes a duration of each first pulse and a number of first pulses per minute, and (b) apply a plurality of second pulses of alternating current between the at least one first electrode element and the at least one second electrode element, wherein the plurality of second pulses has a second set of characteristics that includes a duration of each second pulse and a number of second pulses per minute, and wherein the first and second sets of characteristics are different; and
a controller configured to input data regarding first thermal responses to the plurality of first pulses at the at least one first electrode element and at the at least one second electrode element, and to input data regarding second thermal responses to the plurality of second pulses at the at least one first electrode element and at the at least one second electrode element,
wherein the controller is further configured to select, based on the first and second sets of characteristics, the first thermal responses, and the second thermal responses, a set of characteristics for a plurality of first output pulses of alternating current that (a) maximizes peak current amplitude and (b) keeps temperatures at the at least one first electrode element and at the at least one second electrode element below a threshold value,
wherein the set of characteristics for the plurality of first output pulses includes a duration of each first output pulse and a number of first output pulses per minute.

12. The apparatus of claim 11,
wherein the first set of characteristics further includes a rise time of each first pulse,
wherein the second set of characteristics further includes a rise time of each second pulse, and
wherein the set of characteristics for the plurality of first output pulses further includes a rise time of each first output pulse.

13. The apparatus of claim 11,
wherein the AC voltage generator has a second output configured to (a) apply a plurality of third pulses of alternating current between at least one third electrode element and at least one fourth electrode element, wherein the plurality of third pulses has a third set of characteristics that includes a duration of each third pulse and a number of third pulses per minute and (b) apply a plurality of fourth pulses of alternating current between the at least one third electrode element and the at least one fourth electrode element, wherein the plurality of fourth pulses has a fourth set of characteristics that includes a duration of each fourth pulse and a number of fourth pulses per minute, and wherein the third and fourth sets of characteristics are different,
wherein the controller is further configured to input data regarding third thermal responses to the plurality of third pulses at the at least one third electrode element and at the at least one fourth electrode element, and to input data regarding fourth thermal responses to the plurality of fourth pulses at the at least one third electrode element and at the at least one fourth electrode element,
wherein the controller is further configured to select, based on the third and fourth sets of characteristics, the third thermal responses, and the fourth thermal responses, a set of characteristics for a plurality of second output pulses of alternating current that (a) maximizes peak current amplitude and (b) keeps temperatures at the at least one third electrode element and at the at least one fourth electrode element below a threshold value, and
wherein the set of characteristics for the plurality of second output pulses includes a duration of each second output pulse and a number of second output pulses per minute.

14. The apparatus of claim 13, wherein the number of first pulses per minute is the same as the number of third pulses per minute, wherein the number of second pulses per minute is the same as the number of fourth pulses per minute, and wherein the number of first output pulses per minute is the same as the number of second output pulses per minute.

15. The apparatus of claim 13,
wherein the first set of characteristics further includes a rise time of each first pulse,
wherein the second set of characteristics further includes a rise time of each second pulse,
wherein the third set of characteristics further includes a rise time of each third pulse,
wherein the fourth set of characteristics further includes a rise time of each fourth pulse, wherein the set of characteristics for the plurality of first output pulses further includes a rise time of each first output pulse, and wherein the set of characteristics for the plurality of second output pulses further includes a rise time of each second output pulse.

16. The apparatus of claim 13, wherein the first output of the AC voltage generator is further configured to apply a plurality of fifth pulses of alternating current between the at the least one first electrode element and the at least one second electrode element, wherein the plurality of fifth pulses has a fifth set of characteristics that includes a duration of each fifth pulse and a number of fifth pulses per minute, and wherein the first, second, and fifth sets of characteristics are all different, wherein the controller is further configured to input data regarding fifth thermal responses to the plurality of fifth pulses at the at least one first electrode element and at the at least one second electrode element, and wherein the controller's selection of the set of characteristics for the plurality of first output pulses is further based on the fifth set of characteristics and the fifth thermal responses.

17. The apparatus of claim 11, wherein the first output of the AC voltage generator is further configured to apply a plurality of fifth pulses of alternating current between the at the least one first electrode element and the at least one second electrode element, wherein the plurality of fifth pulses has a fifth set of characteristics that includes a duration of each fifth pulse and a number of fifth pulses per minute, and wherein the first, second, and fifth sets of characteristics are all different, wherein the controller is further configured to input data regarding fifth thermal responses to the plurality of fifth pulses at the at least one first electrode element and at the at least one second electrode element, and wherein the controller's selection of the set of characteristics for the plurality of first output pulses is further based on the fifth set of characteristics and the fifth thermal responses.

18. The apparatus of claim 11, wherein the controller is further configured to select the set of characteristics for the plurality of first output pulses based on a calculation of heat transfer using the equation $$\frac{dQ}{dt} = h \cdot A(T_{body}(t) - T_{env}), \left[\frac{\text{Joule}}{\text{sec}}\right] \text{ or } [\text{Watt}]$$

wherein dQ/dt is the rate of heat transfer out of or into the body, wherein h is the heat transfer coefficient [Watt/k·m$^2$], wherein A is the heat transfer surface area [m$^2$], wherein $T_{body}$ is the temperature of the object's surface, and wherein $T_{env}$ is the temperature of the environment.

* * * * *